United States Patent
Ryan et al.

(10) Patent No.: US 9,078,781 B2
(45) Date of Patent: Jul. 14, 2015

(54) STERILE COVER FOR COMPRESSIBLE STENTS USED IN PERCUTANEOUS DEVICE DELIVERY SYSTEMS

(75) Inventors: Timothy R. Ryan, Shorewood, MN (US); Jack Lemmon, Saint Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 2186 days.

(21) Appl. No.: 11/329,440

(22) Filed: Jan. 11, 2006

(65) Prior Publication Data
US 2007/0162102 A1    Jul. 12, 2007

(51) Int. Cl.
*A61M 5/32* (2006.01)
*A61F 2/958* (2013.01)
*A61F 2/95* (2013.01)

(52) U.S. Cl.
CPC ......... *A61F 2/958* (2013.01); *A61F 2002/9522* (2013.01)

(58) Field of Classification Search
CPC .............. A61M 2005/3134; A61M 2005/3104
USPC ........ 206/571; 604/164.01, 170.02, 171, 192, 604/199
See application file for complete search history.

(56) References Cited

U.S. PATENT DOCUMENTS

| | | | |
|---|---|---|---|
| 565,257 A | 8/1896 | Boyd | |
| 758,195 A | 4/1904 | Schweinert et al. | |
| 1,625,035 A * | 4/1927 | Lilly | 206/571 |
| 2,150,738 A * | 3/1939 | Dunajeff | 604/135 |
| 2,812,231 A * | 11/1957 | Zar | 422/26 |
| 2,986,192 A | 5/1961 | Macleod | |
| 3,334,629 A | 8/1967 | Cohn | |
| 3,409,013 A | 11/1968 | Berry | |
| 3,540,431 A | 11/1970 | Mobin-Uddin | |
| 3,587,115 A | 6/1971 | Shiley | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,714,671 A | 2/1973 | Edwards et al. | |
| 3,731,518 A | 5/1973 | Blocher | |
| 3,755,823 A | 9/1973 | Hancock | |
| 3,795,246 A | 3/1974 | Sturgeon | |
| 3,839,741 A | 10/1974 | Haller | |
| 3,868,956 A | 3/1975 | Alfidi et al. | |

(Continued)

FOREIGN PATENT DOCUMENTS

| DE | 464004 | 8/1928 |
|---|---|---|
| DE | 36 40 745 | 6/1987 |

(Continued)

OTHER PUBLICATIONS

Mechanics of Materials, by Ferdinand P. Beer, E. Russell Johnstonm JR, Apendix B pp. 700 and 702, 2nd Edition, McGraw-Hill Inc., 1992.*

(Continued)

*Primary Examiner* — Jacqueline Woznicki (57) ABSTRACT

A stent cover for enclosing a compressible stent during a stent crimping process, the stent cover having an outer sheath with a proximal end, a distal end, an end portion at the distal end of the sheath having a first diameter, and a stent-retaining portion adjacent to the end portion and having an uncompressed diameter that is larger than the first diameter of the end portion for retaining a stent in its uncompressed condition.

25 Claims, 5 Drawing Sheets

(56) References Cited

U.S. PATENT DOCUMENTS

| | | | |
|---|---|---|---|
| 3,874,388 A | 4/1975 | King et al. | |
| 3,882,866 A * | 5/1975 | Zackheim | 604/193 |
| 3,893,608 A * | 7/1975 | Koenig | 225/1 |
| 4,035,849 A | 7/1977 | Angell et al. | |
| 4,056,854 A | 11/1977 | Boretos et al. | |
| 4,106,129 A | 8/1978 | Carpentier et al. | |
| 4,222,126 A | 9/1980 | Boretos et al. | |
| 4,233,690 A | 11/1980 | Akins | |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,425,908 A | 1/1984 | Simon | |
| 4,434,645 A | 3/1984 | Sverci et al. | |
| 4,470,157 A | 9/1984 | Love | |
| 4,501,030 A | 2/1985 | Lane | |
| 4,574,803 A | 3/1986 | Storz | |
| 4,580,568 A | 4/1986 | Gianturco | |
| 4,592,340 A | 6/1986 | Boyles | |
| 4,610,688 A | 9/1986 | Silvestrini et al. | |
| 4,612,011 A | 9/1986 | Kautzky | |
| 4,647,283 A | 3/1987 | Carpentier et al. | |
| 4,648,881 A | 3/1987 | Carpentier et al. | |
| 4,655,771 A | 4/1987 | Wallsten | |
| 4,662,885 A | 5/1987 | DiPisa, Jr. | |
| 4,665,906 A | 5/1987 | Jervis | |
| 4,710,192 A | 12/1987 | Liotta et al. | |
| 4,733,665 A | 3/1988 | Palmaz | |
| 4,777,951 A | 10/1988 | Cribier et al. | |
| 4,787,899 A | 11/1988 | Lazarus | |
| 4,796,629 A | 1/1989 | Grayzel | |
| 4,797,901 A | 1/1989 | Baykut | |
| 4,819,751 A | 4/1989 | Shimada et al. | |
| 4,834,755 A | 5/1989 | Silvestrini et al. | |
| 4,856,516 A | 8/1989 | Hillstead | |
| 4,872,874 A | 10/1989 | Taheri | |
| 4,878,495 A | 11/1989 | Grayzel | |
| 4,878,906 A | 11/1989 | Lindemann et al. | |
| 4,883,458 A | 11/1989 | Shiber | |
| 4,909,252 A | 3/1990 | Goldberger | |
| 4,917,102 A | 4/1990 | Miller et al. | |
| 4,922,905 A | 5/1990 | Strecker | |
| 4,954,126 A | 9/1990 | Wallsten | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,002,559 A | 3/1991 | Tower | |
| 5,007,896 A | 4/1991 | Shiber | |
| 5,026,366 A | 6/1991 | Leckrone | |
| 5,026,377 A | 6/1991 | Burton et al. | |
| 5,047,041 A | 9/1991 | Samuels | |
| 5,059,177 A | 10/1991 | Towne et al. | |
| 5,061,273 A | 10/1991 | Yock | |
| 5,061,275 A | 10/1991 | Wallsten et al. | |
| 5,074,848 A * | 12/1991 | Burt et al. | 604/263 |
| 5,085,635 A | 2/1992 | Cragg | |
| 5,089,015 A | 2/1992 | Ross | |
| 5,152,771 A | 10/1992 | Sabbaghian et al. | |
| 5,161,547 A | 11/1992 | Tower | |
| 5,163,953 A | 11/1992 | Vince | |
| 5,167,628 A | 12/1992 | Boyles | |
| 5,217,483 A | 6/1993 | Tower | |
| 5,232,445 A | 8/1993 | Bonzel | |
| 5,272,909 A | 12/1993 | Nguyen et al. | |
| 5,295,958 A | 3/1994 | Shturman | |
| 5,327,774 A | 7/1994 | Nguyen et al. | |
| 5,332,402 A | 7/1994 | Teitelbaum et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,415,157 A * | 5/1995 | Welcome | 600/121 |
| 5,431,676 A | 7/1995 | Dubrul et al. | |
| 5,437,083 A | 8/1995 | Williams et al. | |
| 5,443,446 A | 8/1995 | Shturman | |
| 5,464,449 A | 11/1995 | Ryan et al. | |
| 5,480,424 A | 1/1996 | Cox | |
| 5,496,346 A | 3/1996 | Horzewski et al. | |
| 5,500,014 A | 3/1996 | Quijano et al. | |
| 5,507,767 A | 4/1996 | Maeda et al. | |
| 5,534,007 A | 7/1996 | St. Germain et al. | |
| 5,545,209 A | 8/1996 | Roberts et al. | |
| 5,545,211 A | 8/1996 | An et al. | |
| 5,546,646 A | 8/1996 | Williams et al. | |
| 5,554,185 A | 9/1996 | Block et al. | |
| 5,575,818 A | 11/1996 | Pinchuk | |
| 5,580,922 A | 12/1996 | Park et al. | |
| 5,591,195 A | 1/1997 | Taheri et al. | |
| 5,609,626 A | 3/1997 | Quijano et al. | |
| 5,645,559 A | 7/1997 | Hachtman et al. | |
| 5,646,559 A | 7/1997 | Hachtman et al. | |
| 5,667,523 A | 9/1997 | Bynon et al. | |
| 5,672,169 A | 9/1997 | Verbeek | |
| 5,674,277 A | 10/1997 | Freitag | |
| 5,695,498 A | 12/1997 | Tower | |
| 5,713,948 A | 2/1998 | Uflacker | |
| 5,713,953 A | 2/1998 | Vallana et al. | |
| 5,715,723 A | 2/1998 | Owens | |
| 5,725,519 A | 3/1998 | Penner et al. | |
| 5,738,674 A | 4/1998 | Williams et al. | |
| 5,749,890 A | 5/1998 | Shaknovich | |
| 5,766,239 A | 6/1998 | Cox | |
| 5,776,186 A | 7/1998 | Uflacker | |
| 5,782,809 A | 7/1998 | Umeno et al. | |
| 5,800,456 A | 9/1998 | Maeda et al. | |
| 5,817,126 A | 10/1998 | Imran | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,836,952 A | 11/1998 | Davis et al. | |
| 5,840,081 A | 11/1998 | Andersen et al. | |
| 5,855,597 A | 1/1999 | Jayaraman | |
| 5,855,601 A | 1/1999 | Bessler et al. | |
| 5,860,966 A | 1/1999 | Tower | |
| 5,860,996 A | 1/1999 | Tower | |
| 5,861,028 A | 1/1999 | Angell | |
| 5,868,783 A | 2/1999 | Tower | |
| 5,876,448 A | 3/1999 | Thompson et al. | |
| 5,888,201 A | 3/1999 | Stinson et al. | |
| 5,891,191 A | 4/1999 | Stinson | |
| 5,907,893 A | 6/1999 | Zadno-Azizi et al. | |
| 5,911,752 A | 6/1999 | Dustrude et al. | |
| 5,925,063 A | 7/1999 | Khosravi | |
| 5,944,738 A | 8/1999 | Amplatz et al. | |
| 5,947,993 A | 9/1999 | Morales | |
| 5,954,766 A | 9/1999 | Zadno-Azizi et al. | |
| 5,957,949 A | 9/1999 | Leonhardt et al. | |
| 5,968,068 A | 10/1999 | Dehdashtian et al. | |
| 5,984,957 A | 11/1999 | Laptewicz, Jr. et al. | |
| 5,997,573 A | 12/1999 | Quijano et al. | |
| 6,018,857 A | 2/2000 | Duffy et al. | |
| 6,022,370 A | 2/2000 | Tower | |
| 6,027,525 A | 2/2000 | Suh et al. | |
| 6,042,589 A | 3/2000 | Marianne | |
| 6,042,598 A | 3/2000 | Tsugita et al. | |
| 6,051,104 A | 4/2000 | Jang | |
| 6,059,809 A | 5/2000 | Amor et al. | |
| 6,063,102 A | 5/2000 | Morales | |
| 6,074,381 A | 6/2000 | Dinh et al. | |
| 6,090,035 A | 7/2000 | Campbell et al. | |
| 6,110,201 A | 8/2000 | Quijano et al. | |
| 6,123,723 A | 9/2000 | Konya et al. | |
| 6,136,023 A | 10/2000 | Boyle | |
| 6,141,855 A | 11/2000 | Morales | |
| 6,146,366 A | 11/2000 | Schachar | |
| 6,162,208 A | 12/2000 | Hipps | |
| 6,162,245 A | 12/2000 | Jayaraman | |
| 6,168,614 B1 | 1/2001 | Andersen et al. | |
| 6,171,335 B1 | 1/2001 | Wheatley et al. | |

(56) References Cited

U.S. PATENT DOCUMENTS

| | | |
|---|---|---|
| 6,200,336 B1 | 3/2001 | Pavcnik et al. |
| 6,202,272 B1 | 3/2001 | Jackson |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,251,132 B1 | 6/2001 | Ravenscroft et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,110 B1 | 8/2001 | Morales |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,417 B1 | 10/2001 | Spence et al. |
| 6,327,772 B1 | 12/2001 | Zadno-Azizi et al. |
| 6,338,735 B1 | 1/2002 | Stevens |
| 6,348,063 B1 | 2/2002 | Yassour et al. |
| 6,352,547 B1 | 3/2002 | Brown et al. |
| 6,352,708 B1 | 3/2002 | Duran et al. |
| 6,360,577 B2 | 3/2002 | Austin |
| 6,364,870 B1 | 4/2002 | Pinchasik |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,802 B1 | 6/2002 | Yee |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,471,718 B1 | 10/2002 | Staehle et al. |
| 6,475,239 B1 | 11/2002 | Campbell et al. |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,510,722 B1 | 1/2003 | Ching et al. |
| 6,527,800 B1 | 3/2003 | McGuckin, Jr. et al. |
| 6,530,949 B2 | 3/2003 | Konya et al. |
| 6,562,058 B2 | 5/2003 | Seguin et al. |
| 6,569,196 B1 | 5/2003 | Vesely |
| 6,592,546 B1 | 7/2003 | Barbut et al. |
| 6,605,112 B1 | 8/2003 | Moll et al. |
| 6,622,604 B1 | 9/2003 | Chouinard et al. |
| 6,629,350 B2 | 10/2003 | Motsenbocker |
| 6,632,243 B1 | 10/2003 | Zadno-Azizi et al. |
| 6,635,068 B1 | 10/2003 | Dubrul et al. |
| 6,641,609 B2 | 11/2003 | Globerman |
| 6,652,571 B1 | 11/2003 | White et al. |
| 6,652,578 B2 | 11/2003 | Bailey et al. |
| 6,656,213 B2 | 12/2003 | Solem |
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,702,851 B1 | 3/2004 | Chinn et al. |
| 6,716,187 B1 * | 4/2004 | Jorgensen et al. ............ 604/6.05 |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,793 B2 * | 5/2004 | Meyer et al. ............... 604/96.01 |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Streeter et al. |
| 6,773,455 B2 | 8/2004 | Allen et al. |
| 6,786,925 B1 | 9/2004 | Schoon |
| 6,790,229 B1 | 9/2004 | Berreklouw |
| 6,797,002 B2 | 9/2004 | Spence |
| 6,821,297 B2 | 11/2004 | Snyders |
| 6,830,561 B2 * | 12/2004 | Jansen et al. .................. 604/163 |
| 6,830,584 B1 | 12/2004 | Seguin |
| 6,830,585 B1 | 12/2004 | Artof |
| 6,866,650 B2 | 3/2005 | Stevens |
| 6,872,223 B2 | 3/2005 | Roberts |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,929,653 B2 | 8/2005 | Streeter |
| 6,951,571 B1 | 10/2005 | Srivastava |
| 6,989,028 B2 | 1/2006 | Lashinski et al. |
| 7,147,663 B1 | 12/2006 | Berg et al. |
| 2001/0001890 A1 | 5/2001 | Austin |
| 2001/0002445 A1 | 5/2001 | Vesely |
| 2001/0004057 A1 * | 6/2001 | Kempen et al. ............... 206/571 |
| 2001/0007956 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2002/0029014 A1 | 3/2002 | Jayaraman |
| 2002/0029076 A1 | 3/2002 | Yee |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035774 A1 | 3/2002 | Austin |
| 2002/0038144 A1 | 3/2002 | Trout, III et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0138138 A1 | 9/2002 | Yang |
| 2002/0138966 A1 | 10/2002 | Motsenbocker |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0161426 A1 | 10/2002 | Iancea |
| 2002/0163104 A1 | 11/2002 | Motsenbocker et al. |
| 2002/0178566 A1 * | 12/2002 | Reich ............................ 29/426.5 |
| 2002/0193871 A1 | 12/2002 | Beyersdorf et al. |
| 2003/0014104 A1 | 1/2003 | Cribier |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0093086 A1 * | 5/2003 | Briggs et al. .................. 606/108 |
| 2003/0109924 A1 | 6/2003 | Cribier |
| 2003/0125795 A1 | 7/2003 | Pavcnik et al. |
| 2003/0130729 A1 | 7/2003 | Paniagua et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0192164 A1 | 10/2003 | Austin |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |

(56) References Cited

U.S. PATENT DOCUMENTS

| | | |
|---|---|---|
| 2003/0225445 A1 | 12/2003 | Derus et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Seguin et al. |
| 2004/0097788 A1 | 5/2004 | Mourlas et al. |
| 2004/0098112 A1 | 5/2004 | DiMatteo et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0148007 A1 | 7/2004 | Jackson et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2005/0010287 A1 | 1/2005 | Macoviak |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0060029 A1 | 3/2005 | Le |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119722 A1 | 6/2005 | Styrc et al. |
| 2005/0131438 A1 | 6/2005 | Cohn |
| 2005/0137686 A1 | 6/2005 | Salahieh |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0187616 A1 | 8/2005 | Realyvasquez |
| 2005/0203549 A1 | 9/2005 | Realyvasquez |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052750 A1* | 3/2006 | Lenker et al. ............ 604/164.01 |
| 2006/0259134 A1 | 11/2006 | Schwammenthal et al. |
| 2007/0005131 A1 | 1/2007 | Taylor |
| 2007/0016286 A1 | 1/2007 | Herrmann et al. |
| 2007/0027518 A1 | 2/2007 | Case et al. |
| 2007/0088431 A1 | 4/2007 | Bourang et al. |
| 2007/0239271 A1 | 10/2007 | Nguyen |
| 2008/0071362 A1 | 3/2008 | Tuval et al. |
| 2008/0183140 A1* | 7/2008 | Paproski et al. ............ 604/232 |
| 2008/0234797 A1 | 9/2008 | Styrc |

FOREIGN PATENT DOCUMENTS

| | | |
|---|---|---|
| DE | 295 06 654 | 7/1995 |
| DE | 195 32 288 | 3/1997 |
| DE | 195 32 846 | 3/1997 |
| DE | 195 46 692 | 6/1997 |
| DE | 198 57 887 | 7/2000 |
| DE | 199 07 646 | 8/2000 |
| DE | 10049812 | 4/2002 |
| DE | 10049813 | 4/2002 |
| DE | 10049814 | 4/2002 |
| DE | 10049815 | 4/2002 |
| EP | 0144167 | 6/1985 |
| EP | 0 630 623 | 12/1994 |
| EP | 0597967 | 12/1994 |
| EP | 0 701 800 | 3/1996 |
| EP | 0 826 346 | 3/1998 |
| EP | 0850607 | 7/1998 |
| EP | 0 873 731 | 10/1998 |
| EP | 0 935 952 | 8/1999 |
| EP | 0 938 877 | 9/1999 |
| EP | 1057459 A1 | 6/2000 |
| EP | 1057460 A1 | 6/2000 |
| EP | 1088529 | 4/2001 |
| EP | 0937439 B1 | 9/2003 |
| EP | 1340473 | 9/2003 |
| EP | 1356793 | 10/2003 |
| EP | 0819013 | 6/2004 |
| EP | 1472996 | 11/2004 |
| EP | 1229864 B1 | 4/2005 |
| FR | 2788217 | 12/1999 |
| FR | 2 863 160 | 6/2005 |
| GB | 159065 | 2/1922 |
| GB | 2056023 | 3/1981 |
| SU | 1271508 | 11/1986 |
| WO | 90/00098 | 1/1990 |
| WO | 91/17720 | 11/1991 |
| WO | 92/17118 | 10/1992 |
| WO | 93/01768 | 2/1993 |
| WO | 93/15693 | 8/1993 |
| WO | 95/01761 | 1/1995 |
| WO | 95/04556 | 2/1995 |
| WO | 95/29640 | 11/1995 |
| WO | 96/03092 | 2/1996 |
| WO | 96/14032 | 5/1996 |
| WO | 97/03624 | 2/1997 |
| WO | 97/20593 | 6/1997 |
| WO | 98/14137 | 4/1998 |
| WO | 98/19633 | 5/1998 |
| WO | 98/29057 | 7/1998 |
| WO | 98/36790 | 8/1998 |
| WO | 99/12483 | 3/1999 |
| WO | 99/33414 | 7/1999 |
| WO | 99/40964 | 8/1999 |
| WO | 99/47075 | 9/1999 |
| WO | 00/09059 | 2/2000 |
| WO | 00/41652 | 7/2000 |
| WO | 00/44308 | 8/2000 |
| WO | 00/44313 | 8/2000 |
| WO | 00/47136 | 8/2000 |
| WO | 00/47139 | 8/2000 |
| WO | 00/67661 | 11/2000 |
| WO | 00/78248 | 12/2000 |
| WO | 01/05331 | 1/2001 |
| WO | 01/35870 | 5/2001 |
| WO | 01/49213 | 7/2001 |
| WO | 01/54625 | 8/2001 |
| WO | 01/60285 | 8/2001 |
| WO | 01/62189 | 8/2001 |
| WO | 01/64137 | 9/2001 |

(56) References Cited

FOREIGN PATENT DOCUMENTS

| WO | 01/97715 | 12/2001 |
|---|---|---|
| WO | 02/11646 | 2/2002 |
| WO | 02/36048 | 5/2002 |
| WO | 02/41789 | 5/2002 |
| WO | 02/43620 | 6/2002 |
| WO | 02/47575 | 6/2002 |
| WO | 02/060352 | 8/2002 |
| WO | 02/036048 | 10/2002 |
| WO | 02/076700 | 10/2002 |
| WO | 02/100297 | 12/2002 |
| WO | 03/003943 | 1/2003 |
| WO | 03/003949 | 1/2003 |
| WO | 03/011195 | 2/2003 |
| WO | 03/028592 | 4/2003 |
| WO | 03/030776 | 4/2003 |
| WO | 03/037227 | 5/2003 |
| WO | 03/015851 | 11/2003 |
| WO | 03/094793 | 11/2003 |
| WO | 2004/016369 | 2/2004 |
| WO | 2004/019768 | 3/2004 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/047681 | 6/2004 |
| WO | 2004/058106 | 7/2004 |
| WO | 2004/089250 | 10/2004 |
| WO | 2004/089253 | 10/2004 |
| WO | 2004/093728 | 11/2004 |
| WO | 2004/105651 | 12/2004 |
| WO | 2005/002466 | 1/2005 |
| WO | 2005/004753 | 1/2005 |
| WO | 2005/009285 | 2/2005 |
| WO | 2005/011534 | 2/2005 |
| WO | 2005/011535 | 2/2005 |
| WO | 2005/023155 | 3/2005 |
| WO | 2005/027790 | 3/2005 |
| WO | 2005/046528 | 5/2005 |
| WO | 2006/026371 | 3/2006 |
| WO | 2006/134258 | 12/2006 |
| WO | 2007/030825 | 3/2007 |

OTHER PUBLICATIONS

Mechanics of Materials, by Ferdinand P. Beer, E. Russell Johnstonm JR, Apendix B pp. 700 and 702, 2nd Edition, McGraw Hill Inc., 1992.*
Bonhoeffer et al., "Transcatheter Implantation of a Bovine Valve in Pulmonary Position: A Lamb Study," *Circulation Journal of the American Heart Association*, 2000;102;813-816, Mar. 16, 2000.
Bonhoeffer et al., "Percutaneous Insertion of the Pulmonary Valve," *Journal of the American College of Cardiology*, vol. 39, No. 10, 1664-1669, Feb. 20, 2002.
Machine Solutions, Inc. website, MSI equipment, MSI Stent Crimp SC100/150, 2005.
Medtronic, Inc. Instructions for Use Melody™ Transcatheter Pulmonary Valve, pp. 1-4, 2005.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. Volume II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 200, pp. 263-268.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.

(56) References Cited

OTHER PUBLICATIONS

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.

Yonga, et al, "Percutaneous Balloon Mitral Valvotomy: Initial Experience in Nairobi Using a New Multi-Track Catheter System," East African Medical Journal (Kenya), Feb. 1999, pp. 71-74.

Yonga, et al, "Percutaneous Transluminal Balloon Valvuloplasty for Pulmonary Valve Stenosis: Report on Six Cases," East African Medical Journal (Kenya), Apr. 1994, pp. 232-235.

Yonga, et al, "Percutaneous Transvenous Mitral Commissurotomy in Juvenile Mitral Stenosis," East African Medical Journal (Kenya), Apr. 2003, pp. 172-174.

* cited by examiner

STERILE COVER FOR COMPRESSIBLE STENTS USED IN PERCUTANEOUS DEVICE DELIVERY SYSTEMS

TECHNICAL FIELD

The invention relates generally to treatment of cardiac valve disease and more particularly to percutaneous stent and valve delivery systems.

BACKGROUND OF THE INVENTION

Recently, there has been increasing interest in minimally invasive and percutaneous replacement of cardiac valves. Such surgical techniques involve making a very small opening in the skin of the patient into which a valve assembly is inserted via a delivery device similar to a catheter. This technique is often preferable to more invasive forms of surgery, such as opening a large portion of the chest for cardiopulmonary bypass, for example. In the context of pulmonary valve replacement, U.S. Patent Application Publication Nos. 2003/0199971 A1 and 2003/0199963 A1, both filed by Tower, et al., describe a valved segment of bovine jugular vein, mounted within an expandable stent, for use as a replacement pulmonary valve. The replacement valve is mounted on a balloon catheter and delivered percutaneously via the vascular system to the location of the failed pulmonary valve and expanded by the balloon to compress the valve leaflets against the right ventricular outflow tract, anchoring and sealing the replacement valve. As described in the articles: "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits.

As described above, the replacement valves may include a valved vein segment that is mounted in some manner within an expandable stent to make a stented valve. In order to prepare such a valve for percutaneous implantation, the stented valve can be initially provided in an expanded or uncrimped condition, then crimped or compressed around the balloon portion of a catheter until it is as close to the diameter of the catheter as possible. Various methods and devices are available for crimping the stented valve onto the balloon section of the catheter, which may include hand-held devices or tabletop devices, for example. These crimping devices can initially provide an opening that is large enough to accommodate a stented valve in its expanded condition positioned at the balloon section of a catheter. This stented valve can then be compressed by reconfiguring the opening of the crimping device in some way to uniformly decrease the size of the opening until the stented valve is compressed to a desired size.

Because the stented valve and the catheter to which it is mounted must be kept sterile, any crimping device with which the stented valve comes in contact must likewise be sterile. This can be easier to accomplish with hand-held devices than with tabletop devices because hand-held crimping devices can be made to be inexpensive enough that they are provided in a sterile condition and considered to be disposable after a single use (i.e., after crimping a single stented valve onto a balloon portion of a catheter). However, larger valves can require significantly more force for proper compression such that a hand-held device would be difficult or impossible to use. In these cases, or where otherwise desired, larger tabletop crimping devices that can apply more compressive force to the stented valve may be used. These tabletop crimping devices are typically more expensive than disposable devices and they typically must be disassembled, cleaned, and sterilized before and/or after each crimping procedure so that any components with which the valves come in contact will remain sterile. This process of disassembly, cleaning, and sterilizing can be time consuming and expensive, particularly for situations that require significant disassembly of the crimping device. Thus, it is desirable to provide a tabletop crimping configuration that minimizes or eliminates the requirement to repeatedly disassemble and/or sterilize a tabletop crimping device before and/or after each crimping of a stented valve onto a catheter.

SUMMARY OF THE INVENTION

The present invention provides a sterile stent cover for use in crimping or compression operations to eliminate or minimize contact between the components of a crimping device and a stented valve that is being crimped around a balloon or other catheter component. For example, in operations that utilize a tabletop crimping tool, such as the MSI Stent Crimper Model SC100/150, which is commercially available from Machine Solutions, Inc. of Flagstaff, Ariz., an expanded stented valve or other type of stent can be placed within a specifically sized and shaped stent cover of the present invention. The stent cover containing the stented valve can then be positioned over the end of a catheter so that the stented valve is positioned in its desired location along the length of the catheter, such as adjacent to the area of the balloon. Alternatively, a sterile stent or stented valve may be positioned in its desired location along the length of a catheter, and then the stent cover of the present invention can be placed over the top of both the end of the catheter and the stent. In yet another alternative, an expanded stented valve may be placed inside a sterile cover at a remote location within a package that can be removed to expose at least the outer surface of the stent cover to the environment. The stent cover containing the valve can then be positioned over the end of a catheter so that the stent is positioned in its desired location on the catheter. In any of these cases, the inside surface of the sterile stent cover (i.e., the surface that will come in contact with the stented valve), should remain sterile throughout the crimping procedure in order to prevent contamination of the stented valve. This can be accomplished through the use of an end cover removably attached to one end of the stent cover and/or by placing the entire stent cover inside a sterile package, for example.

In any of these cases, a crimping tool or device can then be used in its typical manner to compress the stent, with any crimping surfaces of the crimping tool contacting only the outer surface of the stent cover. It is desirable that the sterile stent cover is made of a material that is strong enough that it does not tear or become otherwise damaged during the crimping operation, but is also preferably thin enough that it does not significantly change the operation of the crimping device or interfere with the crimping process.

With the MSI Stent Crimper set out above, for example, the crimping tool or device includes several adjustable segments positioned around a center opening, with all of the segments being equidistant from that center opening. The center opening is preferably generally annular. To position the adjustable segments in an open configuration of the crimping tool, the segments are simultaneously moved away from the center opening to provide an opening that is large enough to accommodate the stented valve in its uncompressed condition and surrounded by the stent cover. These segments are then simultaneously drawn toward the center opening to reduce the size of the center opening while retaining the generally annular shape of the opening. The size of the stented valve should be reduced to a dimension that is sufficiently small to provide for percutaneous positioning of the valved stent. That is, the crimping tool can precisely reduce the diameter of the stent within the sterile cover to either a fixed diameter over the entire length of the stent or to a stepped diameter, as desired. Because the stent within a stent cover of the invention does not come into contact with any part of the crimping tool during this process, the stent remains sterile, even if the outer surface of the stent cover is not sterile. Thus, the crimping tool advantageously does not need to be cleaned and sterilized after each crimping operation. The stent cover also provides the advantage of keeping the liquid glutaraldehyde solution or other solutions in which tissue valves are stored or rinsed from contacting the crimper parts and causing corrosion and/or contamination of the crimper tool.

The present invention is particularly directed to valves of the type generally described in the Tower et al. and Bonhoeffer, et al. references cited above as used within a prosthetic valve or valve system. However, the invention may also be useful in other types of valves, particularly valves which take the form of a generally tubular valve body of natural or synthetic material, in which valve leaflets are provided. These valves can include stented valves, balloon-expandable valves, and self-expanding valves, for example. In addition, while the invention is described relative to cardiac valves, the stent covers of the invention can similarly be used for other stents or stented components, such as gastric covered stents, abdominal aortic aneurism stents, aortic coarctation stents, coronary stents, neurological stents, or iliac stents, for example.

In one aspect of the invention, a stent cover is provided for enclosing a compressible stent during a stent crimping process. The stent cover has an outer sheath comprising a proximal end, a distal end, an end portion extending from the distal end of the sheath and having a first diameter for at least partially surrounding a tip of a catheter, and a stent-retaining portion adjacent to the end portion and having an uncompressed diameter that is larger than the first diameter of the end portion for retaining a stent in its uncompressed condition, wherein the stent-retaining portion includes a wall at its distal end and adjacent to a proximal end of the end portion. The stent-retaining portion is preferably deformable under pressure from its uncompressed diameter to a compressed diameter that is smaller than the uncompressed diameter while retaining a stent.

The stent cover can further include an end cover that is removably attached to the proximal end of the sheath for preventing contamination of an inner area of the sheath. This end cover can be removably attached to a flange at the proximal end of the sheath. The end cover further can further include an extending tab that extends beyond the flange in at least one location.

The stent cover may further include at least one locator feature for positioning the stent-retaining portion of the sheath relative to a crimping device. The locator feature may be a locating portion of the sheath extending outwardly from the stent-retaining portion, wherein the locating portion of the sheath has a diameter that is larger than the uncompressed diameter of the stent-retaining portion. In particular, the locator feature may be a locator tab extending from an outer surface of the stent-retaining portion or a locator ring extending around the circumference of an outer surface of the stent-retaining portion. The stent cover may also include a locator feature for positioning a stent within the stent-retaining portion of the sheath.

In another aspect of the invention, a method is provided for preparing a compressible stent for percutaneous insertion into an implantation site using an elongated catheter including at least one expandable balloon. The method includes the steps of: providing a stent cover comprising an outer sheath having a proximal end, a distal end, an end portion extending from the distal end of the sheath and having a first diameter for at least partially surrounding a tip of a catheter, and a stent-retaining portion adjacent to the end portion and having an uncompressed diameter that is larger than the first diameter of the end portion for retaining a stent in its uncompressed condition; inserting an uncompressed stent into the stent-retaining area of the sheath; positioning the stent cover and stent so that the uncompressed stent is adjacent to the balloon of the catheter; simultaneously compressing the stent and sheath with a stent-crimping tool; and removing the stent cover. The stent cover can include at least one locator feature for positioning the stent in a desired position within the stent-retaining area of the sheath, The stent cover can also be provided with an end cover releasably attached to the proximal end of the sheath, such that the method further includes the step of removing the end cover prior to inserting an uncompressed stent into the sheath.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF THE PREFERRED EMBODIMENTS

Figure 1:
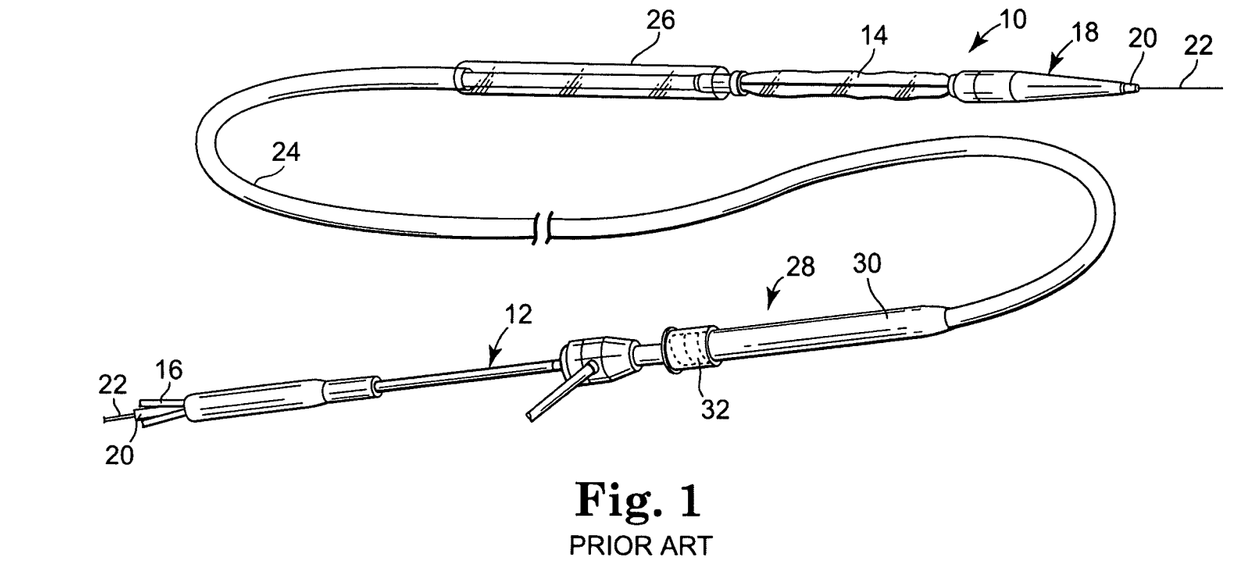
FIG. 1 illustrates a prior art catheter system for percutaneous insertion and implantation of a valve that can be positioned on a balloon of the catheter system according to the methods and devices of the present invention.

Referring now to the Figures, wherein the components are labelled with like numerals throughout the several Figures, and initially to FIG. 1, an exemplary prior art system 10 is illustrated for percutaneous insertion and implantation of a biological venous valvular replacement to a desired implant location, such as the pulmonary vein, a valved conduit or other location, for a defective or malfunctioning valve. System 10 is used for delivering a stented valve to a desired implant location, such as the pulmonary vein, a valved conduit, or other location, where such a system can be utilized with the devices and methods of the present invention. System 10 generally comprises an elongated balloon catheter 12 having an inflatable balloon 14 near the distal end of the system 10. Balloon 14 is connected for fluid communication with a lumen 16 that extends through the length of catheter 12. Lumen 16 provides for inflation and deflation of the balloon 14 with a fluid, such as a radio-opaque fluid, during the process of deploying a stent within a patient. System 10 further includes a tapered tip 18 at its distal end, a centrally located lumen 20, which may be formed from stainless steel tubing, and a thin guide wire 22 that passes through lumen 20. The guide wire 22 may be, for example, a 0.089 cm extra stiff guidewire as manufactured by Amplatzer of Golden Valley, Minn., and be used in a conventional manner to guide the catheter 12 to its desired implant location.

System 10 further includes an elongated sheath 24 positioned over the catheter 12. Sheath 24 is sized so that it can move along the length of the catheter 12, and is provided with a protective shield 26 attached to its distal end. The shield 26 is moveable relative to the balloon 14 by sliding the attached sheath 24 in the desired direction along the catheter 12. FIG. 1 illustrates the sheath 24 in its open position where the balloon 14 is not constrained by the shield 26 and is therefore able to be inflated. Sliding the sheath 24 toward the tapered tip 18 so that shield 26 covers the balloon 14 would provide a closed position of the device 10, which is the configuration in which the device would typically be inserted into a patient. The system 10 may optionally further include a fluid barrier 28 slidably mounted on the proximal end of the sheath 24. The barrier 28 includes a tubular body section 30 and a radially extending end flange 32. This fluid barrier 28 can be positioned within the body lumen with the flange 32 placed in contact against the incision opening to restrict the flow of body fluid through the incision, while allowing the sheath and catheter to be maneuvered within the body lumen and into the implantation site.

Figure 2:
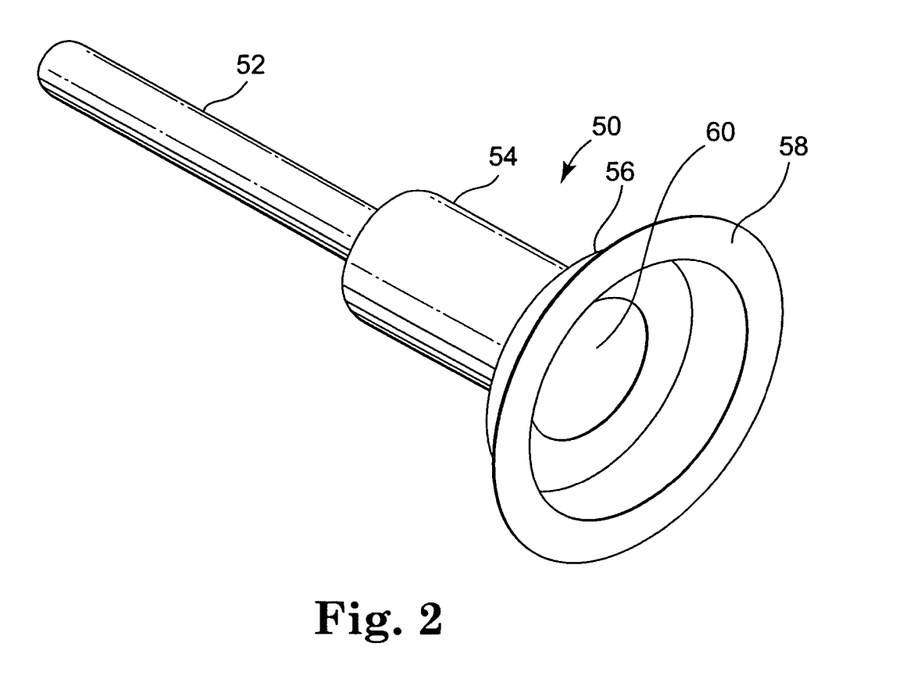
FIG. 2 is a perspective view of one exemplary embodiment of a sterile stent cover in accordance with the present invention.
Figure 3:
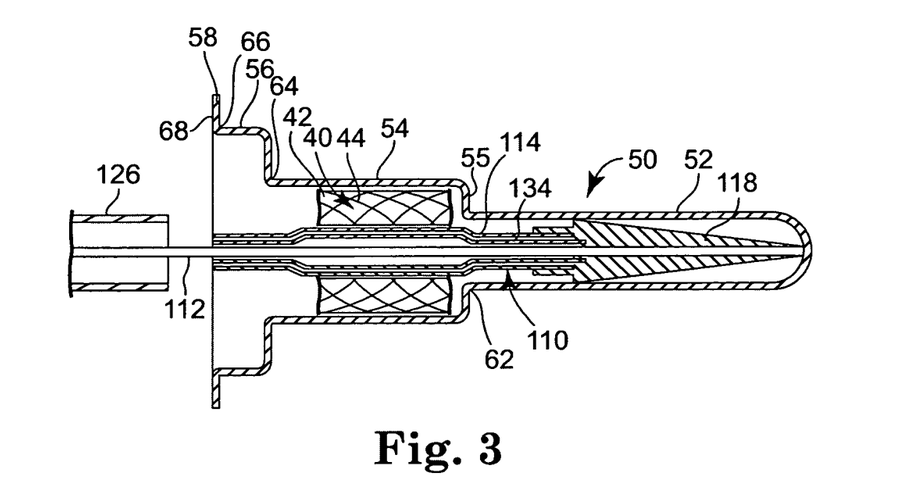
FIG. 3 is a cross-sectional side view of an end portion of a catheter system with one exemplary configuration of a stent cover generally of the type illustrated in FIG. 2 and enclosing a stent in its uncompressed condition.
Figure 4:
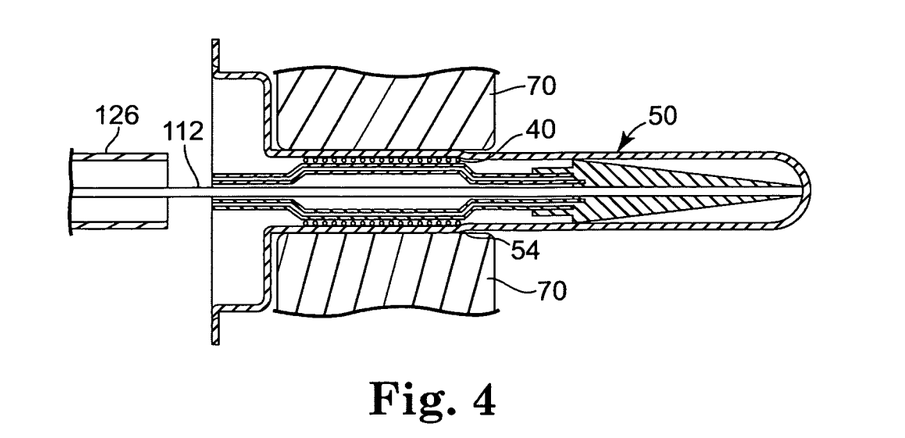
FIG. 4 is a cross-sectional side view of the end portion of a catheter system as illustrated in FIG. 3, and further including a crimper device as it has compressed the stent and stent cover toward the balloon of the catheter system.

Referring now to FIGS. 2-4, one exemplary embodiment of a sterile stent cover 50 of the present invention is illustrated, which generally includes an end portion 52, a stent-retaining portion 54, a locating portion 56, and a flange 58. Stent cover 50 is preferably a single-piece construction, as may be formed by a variety of techniques, such as blow-molding, extrusion, injection molding, thermoforming, and heat shrinking, for example. However, it is also possible that some or all of the segments of the cover 50 are made separately and attached to each other, such as with adhesives. Stent cover 50 further includes a central opening 60 that extends through at least part of the length of stent cover 50 for accepting various portions of a catheter system, such as a balloon catheter system or a catheter system for delivering self-expanding valves and/or stents. In this embodiment, stent cover 50 is essentially a sheath that has a material thickness that is substantially similar for all portions of the cover 50. Thus, the shape of the central opening 60 generally matches the contours of the outer surfaces of stent cover 50 (e.g., the central opening 60 has a smaller diameter in the area of the end portion 52 than in the area of the locating portion 56). The central opening 60 may optionally include multiple ribs spaced from each other around at least a portion of its circumference, such as in an accordion-like arrangement, to promote consistent compression of the stent cover 50.

Stent cover 50 is preferably designed or selected to have certain sizes, shapes, and contours for use with a particular catheter system. For example, stent cover 50 is shown in FIG. 3 as being used with a balloon catheter system 110 generally of the type shown in FIG. 1, where only the distal end portion of the system 110 is shown. In particular, system 110 includes an elongated catheter 112, an outer balloon 114, an inner balloon 134 positioned within outer balloon 114, and a tapered tip 118. A stented valve 40 including a vein segment 42 that is mounted within the interior portion of a stent 44 is prepared at some point prior to surgery for implantation in a particular patient. The stented valve 40 is shown in a location that is adjacent to the outer surface of the outer balloon 114 along the length of the catheter 112 that corresponds with the desired position of the valve 40 for implantation of the valve 40 in a patient. The stented valve 40 is preferably positioned with its entire length adjacent to the balloon 114 so that no portion of the valve 40 extends beyond the length of the balloon 114. The stented valve 40 is further preferably positioned so that it is axially centered relative to the catheter 112. This positioning advantageously allows for relatively uniform expansion of the stented valve within the patient when desired for implantation of the stented valve. The stented valve 40 is shown in its uncrimped or uncompressed condition in this figure, where the inner diameter of valve 40 is at least slightly larger than the outer diameter of the balloon 114.

The stent 44, as shown and described relative to the figures, corresponds generally to a stent of the type described in the above-cited Tower, et al. and Bonhoeffer et al. references, for example, although it is understood that a wide variety of stent configurations can be used in accordance with the invention. The stent 44 may be fabricated of platinum, stainless steel, Nitinol, or other biocompatible metal. Stent 44 may alternatively be fabricated using wire stock as described in the above-cited Tower, et al. applications, or the stent 44 may be produced by machining the stent from a metal tube, as is commonly employed in the manufacturing of stents. The number of wires, the positioning of such wires, and various other features of the stent can vary considerably from that shown in the figures. The stent can be used in conjunction with bovine jugular vein segments in which the stent would typically be in the range of about 16 mm to 20 mm in diameter when expanded. The specifics of the stent can vary widely within the scope of the invention, such that many other known generally cylindrical or cuff-like stent configurations may be used and are considered to be within the scope of the invention. In any case, the stents of the invention are preferably compressible to a relatively small diameter for insertion into a patient, but are also at least slightly expandable from this compressed condition to a larger diameter when in a desired position in the patient. It is further preferable that the process of compressing the stent does not permanently deform the stent in such a way that expansion thereof would be difficult or impossible. That is, the stent should be capable of maintaining a desired structural integrity after being compressed and expanded.

The stent 44, like most expandable and compressible cylindrical stents, generally takes the form of a series of zig-zag ring structures. These structures are coupled longitudinally to one another to form a generally cylindrical-shaped structure, although it is understood that the structures can form be arranged in an at least slightly oval or elliptical shape. Each ring structure takes the form of a series of adjacent generally straight sections that each meet one another at one end at a curved or angled junction to form a "V" or "U" shaped structure. It should also be understood that stents used according to the present invention may employ ring structures coupled to one another at fewer bases of their "V"s or coupled to one another by additional and/or different structures, such as longitudinal members of the type disclosed in U.S. Pat. No. 6,773,455, issued to Allen, et al., U.S. Pat. No. 6,641,609, issued to Globerman, and U.S. Pat. No. 6,136,023, issued to Boyle. The invention also includes within its scope those stents in which wires are formed into zig-zags and wound spirally to produce a cylindrical structure, as in U.S. Pat. No. 6,656,219, issued to Wiktor or woven stents as disclosed in U.S. Pat. No. 4,655,771, issued to Wallsten.

Stents of the type described above, such as can be used with stented valve 40, can be assembled into a pulmonary valve assembly in accordance with the methods of the invention described herein. The pulmonary valve assemblies can be utilized for percutaneous replacement of cardiac valves, for example. One exemplary method for assembling a stented valve generally first includes preparation of a vein segment, then a subsequent mounting or attachment of the prepared vein segment to the stent, using a variety of mounting or attachment techniques. Further, the embodiment illustrated may exemplify a preserved bovine jugular vein of the type described in the above-cited Bonhoeffer, et al. and Tower, et al. references, but other vessels or donor species may alternatively be used.

Referring again to FIG. 3, which shows the components before the crimping operation takes place, stent cover 50 is slid over the catheter 112 until the end portion 52 of cover 50 is in contact with or adjacent to the end of tapered tip 118. In this configuration, end portion 52 extends to cover the tapered tip 118 and may also cover a portion of the balloons 114 and 134. In one preferred positioning of stent cover 50, end portion 52 will be optimally positioned when the inside portion of its tip is in contact with the tapered tip 118. In this way, the person installing the cover 50 will have a tactile indicator of a correct positioning of cover 50. That is, when the person installing the cover feels the inside surface of end portion 52 contacting the end of tapered tip 118, the installer will know that the cover 50 is properly positioned.

The stent-retaining portion 54 preferably has a larger diameter than the end portion 52 in order to provide an internal space that is sufficiently large to contain a stented valve in its uncrimped or uncompressed condition. As shown, stent-retaining portion 54 extends from a shoulder 62, which is provided as a transition between portions 52 and 54, to another shoulder 64, which is provided as a transition between portions 54 and 56. The length of stent-retaining portion 54 is preferably large enough that it encloses the entire length of the stented valve 40 in its uncrimped condition, and even more preferably also has a sufficient length to enclose the entire length of the stented valve 40 when it is in its compressed condition. Thus, at least a portion of the balloon 114 is also preferably surrounded by the stent-retaining portion 54. Stent-retaining portion 54 further includes a wall 55 extending from shoulder 62 to the outer wall of portion 54. The wall 55 defines a distal edge of the stent-retaining portion 54 and is preferably configured to prevent a stent enclosed within the portion 54 from moving into the end portion 52. That is, the wall 55 can be used to position a stent in its desired position along the length of a catheter (e.g., so that it is positioned adjacent to a balloon or balloons that will be used to expand the stent). The wall 55 can be generally perpendicular to the central axis of the stent cover 50, as shown, or may instead be at a different angle and/or the wall may provide an area where the end portion 52 tapers from its smaller diameter up to the larger diameter of the stent-retaining portion 54.

The locating portion 56 of stent cover 50 has a larger diameter than the stent-retaining portion 54, although it is possible that the locating portion 56 is essentially an extension of the stent-retaining portion 54 that has essentially the same diameter as the stent-retaining portion 54. However, in the embodiment of FIG. 3, the locating portion 56 extends from the shoulder 64 to another shoulder 66 provided as a transition between locating portion 56 and flange 58. Locating portion 56 can be used to provide a physical locator for proper placement of the stent cover 50 relative to a crimping device, as will be described in further detail below. Flange 58 can have a relatively small length or thickness as compared to lengths of the portions 52, 54, and 56 of the stent cover 50. In fact, as can be seen in FIGS. 2 and 3, the flange 58 can have a thickness that essentially corresponds with the thickness of the material from which the stent cover 50 is made. Flange 58 includes a face surface 68 that extends as a ring around the outer circumference of flange 58.

Each of the shoulder portions 62, 64, and 66 described above are provided as areas for smooth transitions between portions of the stent cover 50 having different diameters. As shown, the shoulder portions 62, 64, and 66 have a small radius, although it is possible to instead have sharp corners at some or all of these transition points. In some cases, the use of a small radius at the shoulder areas can lessen stress concentrations that might otherwise cause cracking or other damage to the stent cover 50 as it is manipulated for the installation and crimping processes. These shoulder portions 62, 64, and 66 can optionally have an increased material thickness to provide additional strength in these areas. Each of the shoulder portions 62, 64, and 66 can have the same or different configurations relative to the other shoulder portions.

Figure 5:
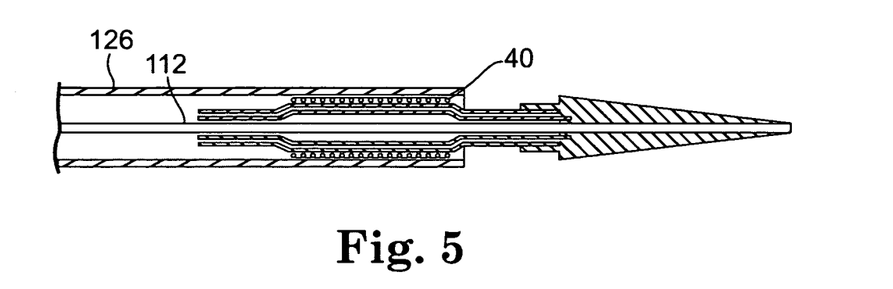
FIG. 5 is a cross-sectional side view of the end portion of a catheter system as illustrated in FIG. 4, with the stent in its compressed condition and with the stent cover removed, and further illustrating a shield positioned to cover the compressed stent.

After the stent cover 50 is properly positioned to cover the stented valve 40, the entire catheter assembly can then be positioned for compression relative to a crimping device or tool. FIG. 4 illustrates compression components 70 of a crimping tool in a position in which they are being pressed or moved toward each other to compress the stented valve 40 toward the catheter 112. The compressive force is preferably relatively uniform about the circumference of the stented valve 40 and the stent-retaining portion 54. The compressive force is also applied in such a way that the wires of the stent are uniformly deformed and not otherwise undesirably deformed. When the desired amount of compression is completed, the stent cover 50 can be removed. As shown in FIG. 5, sheath 126 may then be moved to cover and contain the compressed stented valve 40, thereby preventing unintentional expansion and/or migration of the stent or stented valve 40, and providing a smooth surface for insertion of the catheter system into a patient. Sheath 126 may be moved to cover either more or less of the catheter system than shown, as desired.

With any of the devices or methods of the invention, it is possible that the crimping operation takes place in one or more steps, and may be performed with a single device or multiple devices. In addition, the crimping process may be performed completely or partially by hand, where a person's fingers may manipulate the outside surface of the stent cover without compromising the sterile condition of a stent contained within the cover. It is further contemplated that the stent covers of the invention can be provided with perforations or tear tabs to allow for easier removal of the stent cover from the catheter assembly. Such relief or weakened areas on the stent cover can have a wide variety of configurations and should be easily operable by the person desiring to remove the stent cover One exemplary use of such a feature on a stent cover is to allow an operator to easily tear the stent cover into two or more pieces, such as with a tear strip that extends along the length of the stent cover on one or both sides of the stent cover.

Figure 6:
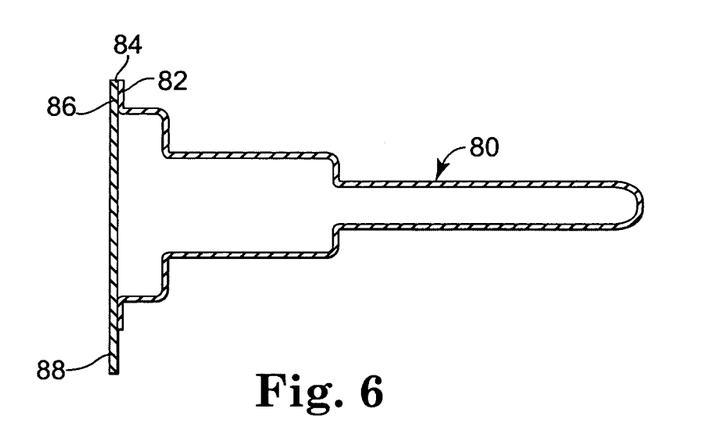
FIG. 6 is a cross-sectional side view of another exemplary stent cover in accordance with the invention, further including an end cover.

The flange face surface of the stent covers of the present invention, such as face surface 68 of FIG. 3, can be designed to provide a large enough surface area for attachment of other materials. In many cases, it is thus advantageous for the flange face surface to be relatively planar and smooth. For example, FIG. 6 illustrates another exemplary embodiment of a stent cover 80 having a flange 82 with a face surface 86 and an end cover 84 secured to the face surface 86. End cover 84 can be attached to the flange 82 by any known method, depending on the materials chosen for the flange and cover. The type of securing process chosen should correspond with providing a desired seal strength between the flange 82 and end cover 84. The desired seal strength between the flange 82 and end cover 84 preferably provides a seal that does not permit outside contaminants to enter the inner area of the stent cover 80, yet can provide a breakable seal that allows the end cover 84 to be peeled away from the face surface 86 without destroying the end cover 84 and/or any portion of stent cover 80 to which it is attached (e.g., the flange 82). For example, end cover can be secured to the flange 82 with an adhesive that is placed on the surface of the flange 82 and/or the end cover 84 before pressing the surfaces together. In another example, the end cover 84 can be heat sealed to the flange 82.

The end cover 84 and flange 82 may be made of the same or different materials, where one contemplated embodiment of the invention includes using a stent cover 80 with a flange 82 made of a thin, flexible plastic material and an end cover 84 made of a foil backed paper. One specific example of a material that can be used for end cover 84 is a protective material commercially available under the trade name "Tyvek" from Dupont, of Wilmington, Del. This material advantageously is lightweight, strong, and vapor-permeable, while also being resistant to water, chemicals, punctures, tears, and abrasion. This material or similar materials can be used for the end cover 84 to prevent contaminants from entering the inner area of stent cover 80, but to also allow for entry of a sterilant gas into the inner area of stent cover 80 to kill bacteria and/or other contaminants without removal of the end cover 84, when desired.

The end cover 84 may be sized and shaped to closely match the outside perimeter of the flange 82, or may include an extending tab 88 that extends beyond the outer edge of the flange 82. Extending tab 88 provides a surface that can be gripped by fingers or a gripping device as a starting point to peel the end cover 84 away from the flange 82, thereby providing quick and easy access into the inner area of stent cover 80. Extending tab 88 may extend beyond the edge of flange 82 in one or more discrete areas around the perimeter of the flange 82. Alternatively, the end cover 84 can be made large enough that it extends beyond the edge of flange 82 around all or most of the outside perimeter of the flange 82 so that the user can essentially grasp the end cover 84 at any point where it extends beyond flange 82 to pull it from the stent cover 80.

Stent covers that are provided with an end cover, such as stent cover 80, will preferably have an interior area that is sterile once the end cover 84 is removed, such as immediately prior to a surgical procedure. In this way, the stent cover will not compromise the sterility of a stent that is to be implanted in a patient via a catheter system. The outside of such a stent cover is not necessarily sterile, which may be an acceptable situation because the outer surface of the stent cover may come into contact with a crimping device that is also not sterile. As described above, the fact that the crimping device surfaces that contact the outer surface of a stent cover of the invention do not need to be sterile is one of the advantages provided by the stent covers of the present invention. However, if it is desired for the outer surface of the stent cover to also be sterile, the stent cover can be stored within a separate pouch or container that maintains the stent in a sterile condition until that pouch or container is opened. In this case, the use of an end cover may not be necessary, although it is still possible to use such an end cover. Further, if a valve is being used that can be kept within a container for a relatively extended time period before being used in a surgical procedure (e.g., polymer leaflet valves), the valve itself may be stored and shipped within a sterile inner area of a stent cover. This stent cover can then be sealed with an end cover and/or placed in a sterile pouch, as described above.

Figure 7:
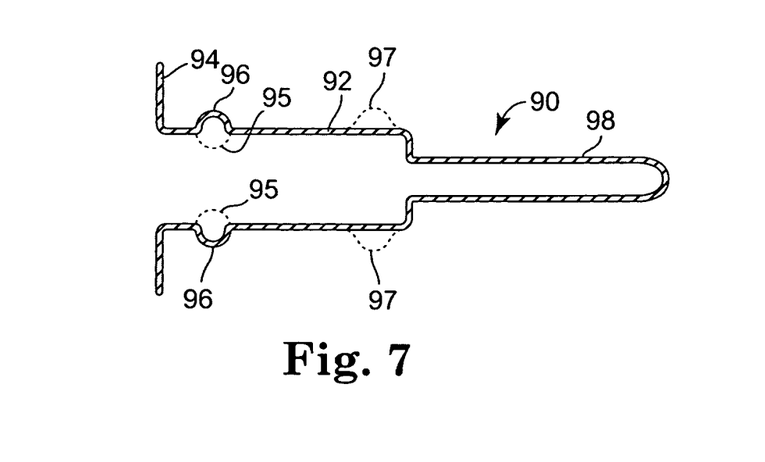
FIG. 7 is a cross-sectional side view of another exemplary stent cover including at least one extension from its outer surface.

FIG. 7 illustrates another exemplary embodiment of a stent cover 90 in accordance with the invention. Stent cover 90 includes a stent-retaining portion 92 extending between a flange 94 and an end portion 98. Stent-retaining portion 92 is essentially cylindrical except for the inclusion of at least one locator tab 96 extending from its outer surface. Locator tabs 96 can provide a guide for proper positioning of the stent cover 90 in a crimping device. For example, the crimping device may desirably be positioned so that its contact surfaces are positioned at a particular distance from locator tabs 96, but so that the contact surfaces of the crimping device do not contact the tabs 96 during the crimping operation.

Locator tabs 96 can be provided as relatively rigid portions of the portion 92 that can take a wide variety of shapes. Tabs 96 may have a size and shape different from those shown in the drawings, such as triangular, rectangular, irregular, or the like. In addition, locator tabs 96 may be temporarily or permanently deformable so that they can be depressed inwardly, such as is illustrated by the exemplary location shown as dotted line 95. If the locator tabs 96 are deformed in this way, the portion of the tabs 96 that extend inwardly (e.g., as shown by dotted line 95) into the stent-retaining portion 92 can help to keep an enclosed stent in its desired location. In particular, the tabs 96 can be depressed after a stent is inserted into the interior area of stent cover 90 so that the inwardly extending locator tabs 96 can prevent backward migration of an enclosed stent. In a further alternative, locator tabs 96 may instead comprise a continuous extending ring around the circumference of the interior area of stent-retaining portion 92, where the entire ring can be depressed inwardly, or only certain portions of the ring are inwardly deformable.

Stent cover 90 may alternatively or additionally be provided with locator tabs 97 that are adjacent to the end portion 98 and spaced from any locator tabs 96 along the length of stent-retaining portion 92. These locator tabs 97 can be provided with the same or similar features as described above relative to locator tabs 96. Locator tabs 97 may be used alone or in combination with any locator tabs 96 to assist in accurate positioning of the stent cover 90 relative to the jaws of a crimping device and/or to assist in accurate positioning of a stent within the stent-retaining portion 92 (e.g., if the locator tabs 97 are depressed so that they extend inwardly into the stent cover 90).

As yet another alternative, the stent covers of the invention may include locator markings in addition to or instead of locator tabs to provide a guide for proper positioning of the stent cover in a crimping device and/or for proper positioning of a stent within a cover. If such markings are used, one or more markings may be used on each stent cover, depending on the particular positioning guidance that is desired. For example, multiple markings may be provided on a particular stent cover to accommodate stents of different sizes, where each individual marking corresponds to a stent of a certain size. If markings and locator tabs are both provided on a single stent cover, the markings may be in the same or different locations from the locator tabs. Markings may also be used with any of the other features of the stent covers of the invention. Such markings can include any type of visual or tactile indicator that differentiates the marking from the cover material, such as colored strips, raised bumps, depressed areas, or the like.

Figure 8:
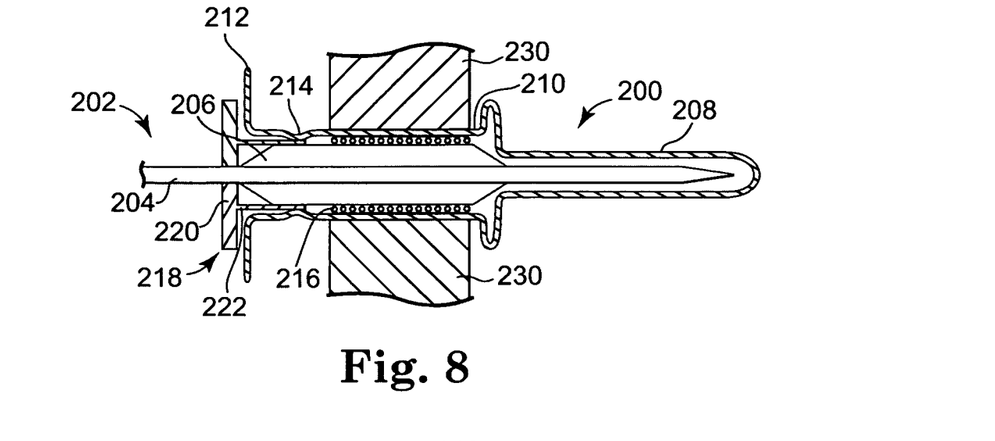
FIG. 8 is a cross-sectional side view of another exemplary stent cover positioned over a portion of a catheter system and a stent, and further including a locator feature to assist in proper positioning of the stent relative to the stent cover.

FIG. 8 illustrates another exemplary embodiment of a stent cover 200 of the invention, as positioned over a catheter system 202 that generally comprises an elongated catheter 204 and an expandable portion 206. Stent cover 200 includes an end portion 208, a stent-retaining portion 210, and a flange 212. Stent-retaining portion 210 and its enclosed stent 216 are shown as being at least partially compressed toward the catheter 204 by the compression surfaces 230 of a crimping device.

Stent-retaining portion 210 extends between flange 212 and end portion 208, and is essentially cylindrical except for the inclusion of at least one locator tab 214 extending into the interior portion of the stent-retaining portion 210. Locator tabs 214 can provide a guide for proper positioning of the stent 216 within the stent-retaining portion 210 and may include one or a series of discrete tabs, or may include a continuous depression around the inner circumference of the stent-retaining portion 210. This stent cover 200 is further provided with a retainer sleeve 218 that includes a base 220 from which an extending ring 222 protrudes. The retainer sleeve 218 is preferably provided as a sterile component and is configured to keep the stent 216 retained within the stent cover 200 during the crimping operation. Thus, extending ring 222 preferably is sized and shaped in such a way that it can obstruct movement of the stent 216 toward the flange 212 when being compressed by the compression surfaces 230. The extending ring 222 can further include a contoured surface or other feature (not shown) that can engage with at least one locator tab 214 of the stent-retaining portion 210 for positive engagement between the extending ring 222 of the retainer sleeve and at least one locator tab 214. This can provide additional assurance that the stent 216 is properly positioned relative to the catheter system 212.

Figure 9A:
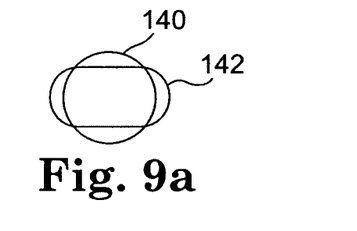
FIGS. 9a-9c illustrate schematic top views of another exemplary stent cover of the invention that is elastically deformable to provide an interference fit between the stent cover and a stent positioned therein.
Figure 9B:
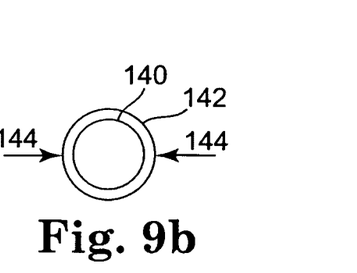
Figure 9C:
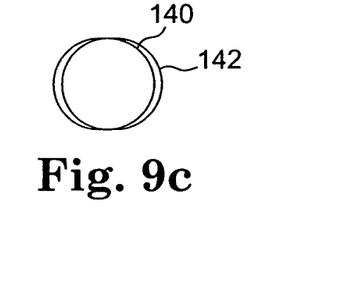

Another way of holding a stent cover of the invention firmly against a stent to prevent migration of the stent before or during the crimping operation includes using a stent cover that is not cylindrical in shape unless deformed. For example, the stent cover may be oval or elliptical in shape, and made of an elastic material with a memory so that it returns to its original shape after being deformed. A schematic view of this arrangement is illustrated in FIGS. 9a-9c. In particular, FIG. 9a shows a stent 140 having a relatively cylindrical circumference as superimposed on the end view of a stent cover 142 that is oval or elliptical in shape when in its undeformed condition. The stent cover 142 is deformed by compressive forces 144 shown in FIG. 9b to change the shape of cover 142 to be relatively cylindrical or circular and/or to match the general shape of a stent that will be positioned therein. The stent cover 142 can then be positioned over the stent 140 and the compressive forces 144 on the cover 142 can be released. Due to the elastic properties of the cover 142, it can relax and move back toward its original oval or elliptical shape until it contacts the stent 140, as shown in FIG. 9c. This provides an interference-type fit between the stent 140 and the stent cover 142 to prevent migration of the stent cover 142 relative to the stent 140. It is preferable, however, that the stent cover 142 does not deform the stent 140 significantly when it returns to its original shape.

Any of the stent covers of the present invention can have elastic material properties similar to that of a latex glove and are preferably transparent or translucent to allow for viewing of the stent location relative to the cover before, during, and/or after the crimping operation. The stent covers are preferably constructed of materials that are capable of being sterilized and containing a valved stent without causing contamination of the stent. For example, the stent cover material may be made of PTFE, polypropylene, polyethylene, polyurethane, latex, nylon elastomers, or nitrile, for example, and may include any thin-walled heat shrink tubing that is relatively compliant for conforming to the shape of the stent as it is compressed. One particular example of an appropriate material for the stent covers of the invention is the Ultra Thin Wall Polyester (PET) Heat Shrink Tubing commercially available from Advanced Polymers Incorporated of Salem, N.H. The stent covers can include relatively smooth, flat interior and exterior surfaces, or may instead be textured so that they are easier for a user to grip. The stent covers may also comprise an expandable structure, such as an accordion-like structure, that allows a large amount of collapsibility of the stent cover during the crimping procedure.

In another alternative embodiment of the invention, the stent covers can be attached via a fitting or other configuration to a device that can extract air from the stent cover. That is, a level of vacuum can be drawn that is sufficient to remove air from the stent cover and collapse the cover uniformly during the crimping operation.

In a preparation for a surgical procedure using a catheter system of the type illustrated in FIG. 1, for example, a stented valve is prepared and provided, along with a corresponding sterile stent cover of the type described herein in accordance with the present invention. If the stent cover is provided with an end cover of the type illustrated in FIG. 6, this end cover should be peeled back to expose the interior area of the sterile stent cover. The stented valve can then be positioned either over the balloon of the catheter system or inside the sterile stent cover. In either case, the stent cover is then positioned on the end of the catheter system as described herein, with the stent in its uncrimped or uncompressed condition and positioned over a balloon of the catheter system. The stent cover with a stented valve positioned therein is placed within the jaws or compression surfaces of a crimping device. If the stent cover includes locator features, these features can be used to verify the location of the stent cover relative to the crimping device.

The stented valve can then be compressed within the sterile stent cover around a single or double balloon located on the inner balloon catheter of the type illustrated in FIG. 1, as described above. The sterile cover may then be removed and a shield or other protector can be positioned to cover the compressed stent. The delivery system and its use may correspond to that described in the above-cited Tower, et al. applications. The delivery system is advanced to the desired valve implant site using a guidewire, for example, with the shield positioned over the compressed stent. The shield can then be retracted to allow balloon expansion of the stented valve. That is, the shield is moved proximally, exposing the stent positioned over the balloon, which can then be expanded. The expansion of the balloon causes a corresponding expansion of the stented valve against the inner surface of the previously implanted adapter stent, stabilizing and sealing the stented valve within the adapter stent. The balloon can then be deflated and the delivery system withdrawn proximally.

It is contemplated that the stent covers of the present invention can be used with different types of catheter systems than the general type of system illustrated in FIG. 1. For example, the stent covers of the invention can be used with stents that can expand without the use of a balloon, such as stents of the type commonly known as self-expanding stents. In this case, a self-expanding stent can be positioned in its desired location along the length of a catheter and within a stent cover. The stent and stent cover can then be compressed by a crimping device and the stent cover can be partially withdrawn to allow the compressed stent to be transferred under a delivery catheter sheath to prevent it from expanding. The sheath can later be retracted once the device is properly positioned for deployment of the stent within the patient, thereby allowing the stent to expand on its own.

It is further contemplated that the stent covers of the invention can be used with polymer or Nitinol mesh leaflet valves, or any type of valve that can be attached to a compressible stent. That is, the stent covers of the present invention are not limited to use with devices in the treatment of cardiac valve disease, but can also be useful in any surgical procedure that involves the use of a compressible stent that needs to be kept sterile while being compressed at least slightly. For example, the stent covers of the invention can be used in the compression of relatively large stents, such as covered and uncovered aortic coarctation stents, gastric covered stents, and abdominal aortic aneurism stents such as the stents used in the Talent™ AAA Stent Graft System, which is commercially available from the assignee of the present invention.

In the case of a stented valve made using bovine jugular vein or other preserved biological tissue, the stented valve can be sterilized, stored and shipped separately in a buffered glutaraldehyde solution, but typically will not be pre-mounted on the delivery system. This stented valve may also be provided in combination with a sterile cover within a single package, where the stented valve can be positioned within a recess in the sterile cover, for example. However, it is possible that the stented valve can also be pre-mounted on the delivery system if the system with a valve mounted thereon is similarly sterilized and kept in a sterile environment. In this case, a sterile cover may be placed over the end of the delivery system in accordance with the invention immediately prior to the crimping operation, which may occur before packaging or may occur in or near the operating room. That is, the implanting physician or an assistant may perform the step of mounting the stented valve to the balloon and performing the crimping operation, with the sterile cover placed over the stented valve in accordance with the invention. It is further understood that the sterile cover can be used as a rinse container for rinsing the valve in preparation for positioning it on the delivery system. In yet another alternative, the valve can be shipped in its expanded condition within a valve cover containing a liquid sterilant or preservation solution (e.g., a buffered glutaraldehyde solution). The stent cover would then be drained and the valve would be rinsed prior to compression of the valve.

The present invention has now been described with reference to several embodiments thereof. All patents, patent applications, publications and journal articles mentioned herein are incorporated herein by reference in their entirety. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A stent cover for enclosing a compressible stent during a stent crimping process, the stent cover comprising an outer sheath having a single-piece construction and comprising:
    a proximal end;
    a closed distal end;
    a generally cylindrical end portion extending from the closed distal end of the sheath toward the proximal end and having an inner diameter for at least partially surrounding a tip of a catheter;
    a generally cylindrical stent-retaining portion adjacent to the end portion and having an uncompressed inner diameter that is larger than the inner diameter of the end portion for retaining a stent in an uncompressed condition;
    a locating portion adjacent to the stent-retaining portion and having a larger inner diameter than the uncompressed inner diameter of the stent-retaining portion; and
    a flange extending from a proximal end of the locating portion, wherein the flange extends beyond an outer diameter of the locating portion at the proximal end of the sheath.

2. The stent cover of claim 1, wherein the sheath further comprises a wall adjacent to a proximal end of the end portion, wherein the wall extends generally perpendicular to an outer cylindrical surface of the end portion.

3. The stent cover of claim 1, wherein the sheath further comprises a wall adjacent to a proximal end of the end portion, wherein the wall extends at an angle from the end portion toward the stent-retaining portion.

4. The stent cover of claim 1, wherein the stent-retaining portion is radially deformable under pressure from its uncompressed diameter to a compressed diameter that is smaller than the uncompressed diameter while retaining a stent.

5. The stent cover of claim 1, wherein the sheath further comprises an inner area that is substantially sterile.

6. The stent cover of claim 1, further comprising an end cover removably attached to a face surface of the flange at the proximal end of the sheath for preventing contamination of an inner area of the sheath.

7. The stent cover of claim 6, wherein the end cover further comprises an extending tab that extends beyond and is spaced from the outer edge of the flange.

8. The stent cover of claim 6, further comprising a sterile solution contained within the inner area of the sheath.

9. The stent cover of claim 1, wherein the flange comprises a generally planar ring that extends circumferentially around the proximal end of the sheath.

10. The stent cover of claim 9, further comprising an end cover releasably attached to at least a portion of the generally planar ring of the flange.

11. The stent cover of claim 10, wherein the end cover is adhered to at least a portion of the flange.

12. The stent cover of claim 10, wherein the end cover further comprises an extending tab that extends beyond the planar ring of the flange in at least one location.

13. The stent cover of claim 1, in combination with a stented valve positioned within the stent-retaining portion, wherein the stented valve comprises a valve segment secured within a stein frame.

14. The stent cover of claim 13, wherein the valve segment comprises a polymer valve.

15. The stent cover of claim 13, wherein the valve segment comprises a nitinol mesh valve.

16. The stent cover of claim 1, further comprising at least one locator feature for positioning the stent-retaining portion of the sheath relative to a crimping device.

17. The stent cover of claim 16, wherein the at least one locator feature comprises a locating portion of the sheath extending outwardly from the stent-retaining portion, wherein the locating portion of the sheath has a diameter that is larger than the uncompressed diameter of the stent-retaining portion.

18. The stent cover of claim 16, wherein the at least one locator feature comprises a locator tab extending from an outer surface of the stent-retaining portion.

19. The stent cover of claim 16, wherein the at least one locator feature comprises a locator ring extending around the circumference of an outer surface of the stent-retaining portion.

20. The stent cover of claim 16, wherein the at least one locator feature is depressible into an interior space of the stent-retaining portion for positioning a proximal end of a stent within the stent-retaining portion of the sheath.

21. The stent cover of claim 16, wherein the at least one locator feature comprises an area of the stent cover that is visually distinct from the remainder of the stent cover.

22. The stent cover of claim 16, wherein the at least one locator feature comprises an area of the stent cover that is tactilely distinct from the remainder of the stent cover.

23. The stent cover of claim 1, further comprising a locator feature for positioning a stent within the stent-retaining portion of the sheath.

24. The stent cover of claim 1, wherein the stent-retaining portion is radially deformable from an uncompressed diameter to a smaller diameter in response to at least one external force.

25. The stent cover of claim 1, in combination with a catheter system for percutaneously inserting a stent in an implantation site, the catheter system comprising an elongated catheter with an inflatable balloon located adjacent to its distal end, a stent positioned to at least partially surround the inflatable balloon, and a protective shield slideably mounted for movement between a position where it can cover the balloon and stent to a position where the balloon and stent can be expanded, wherein the stent cover is positioned so that the stent-retaining portion of the sheath at least partially surrounds the stent.

* * * * *